US00PP23731P3

(12) United States Plant Patent
Adam, Jr.

(10) Patent No.: US PP23,731 P3
(45) Date of Patent: Jul. 9, 2013

(54) ***CHRYSANTHEMUM* PLANT NAMED 'AUTUMN MOON'**

(50) Latin Name: *Chrysanthemum×morifolium*
Varietal Denomination: Autumn Moon

(75) Inventor: Sinclair A Adam, Jr., St. Albans, VT (US)

(73) Assignee: Vermont Organics Reclamation Inc, Williston, VT (US)

( * ) Notice: Subject to any disclaimer, the term of this patent is extended or adjusted under 35 U.S.C. 154(b) by 185 days.

(21) Appl. No.: 13/134,605

(22) Filed: Jun. 10, 2011

(65) Prior Publication Data

US 2012/0317688 P1 Dec. 13, 2012

(51) Int. Cl.
*A01H 5/00* (2006.01)

(52) U.S. Cl.
USPC ..... Plt./289

(58) Field of Classification Search
USPC ..... Plt./289
See application file for complete search history.

*Primary Examiner* — Annette Para
(74) *Attorney, Agent, or Firm* — AKC Patents LLC; Aliki K. Collins

(57) ABSTRACT

A new cultivar of *chrysanthemum* plant botanically known as *Chrysanthemum×morifolium,* and commercially referred to by the varietal name 'Autumn Moon'. The new cultivar has a single flower form with pale yellow ray florets and a hint of pink in the ray florets, uniform habit and flowering response that is late, strong stems, medium green foliage color, good garden habit, and excellent shelf life.

3 Drawing Sheets

Latin name of the genus and species of the plant named: *Chrysanthemum×morifolium.*

Variety denomination: 'Autumn Moon'.

FIELD OF THE INVENTION

The present invention relates to a new *Chrysanthemum* plant botanically known as *Chrysanthemum×morifolium,* and hereinafter referred to by the varietal name 'Autumn Moon'.

BACKGROUND OF THE INVENTION

'Autumn Moon' is a product of a planned breeding program that focuses on obtaining new cultivars of garden *chrysanthemums* in a range of flower colors that bloom late in the season after other fall mums have passed. These plants exhibit superior winter hardiness suitable for northern climates and provide much needed food for bees and beneficial insects.

'Autumn Moon' originated from an open pollinated cross in 2005 at Dunvegan Nursery in Coatesville, Pa. The female parent was the species *Chrysanthemum indicum*, a semi-double daisy form with yellow and pink ray florets, and medium upright habit. The male parent of 'Autumn Moon' is *Chrysanthemum×koreanum* 'Sheffield', with single flowers of pink floret color, and a well-branched habit, producing an abundant amount of pollen. 'Autumn Moon' was selected as one flowering plant within the progeny of the stated cross in November 2005, and grown out of doors in Coatesville, Pa.

The first act of asexual reproduction of 'Autumn Moon' was accomplished when vegetative cuttings were propagated from the initial selection in April 2008, in a controlled environment in Coatesville, Pa.

SUMMARY OF THE INVENTION

'Autumn Moon' has a single flower form with pale yellow ray florets and a hint of pink in the ray florets, uniform habit and flowering response that is late, strong stems, medium green foliage color, good garden habit, and excellent shelf life.

Horticultural examination of plants grown from cuttings of the plant initiated in April 2008 and continuing thereafter, has demonstrated that the combination of characteristics as herein disclosed for 'Autumn Moon' are firmly fixed and are retained through successive generations of asexual reproduction.

'Autumn Moon' has not been observed under all possible environmental conditions. The phenotype may vary significantly with variations in environment such as temperature, light intensity and day length.

'Autumn Moon' has not been made publically available for more than one year prior to this filing.

The following traits have been repeatedly observed and are determined to be basic characteristics of the new variety. The combination of these characteristics distinguishes 'Autumn Moon' from all other varieties of *chrysanthemum* known to the inventors.

BRIEF DESCRIPTION OF THE PHOTOGRAPHS/DRAWINGS

The accompanying photographic drawing shows typical flower and foliage characteristics of 'Autumn Moon' with colors being as true as possible with an illustration of this type.

DETAILED BOTANICAL DESCRIPTION

Figure 1:
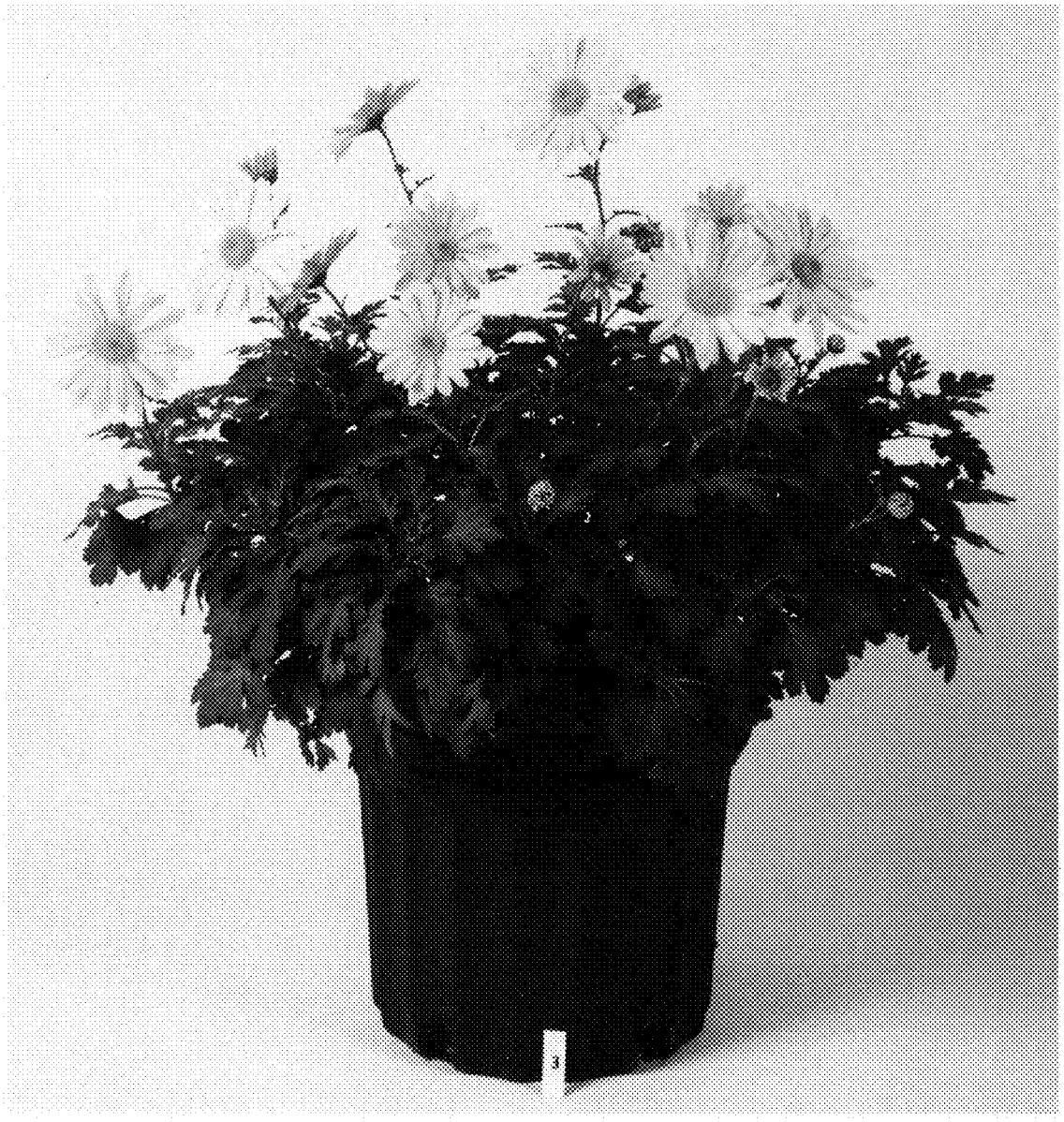
FIG. 1 shows a plant of the cultivar in full bloom.
Figure 2:
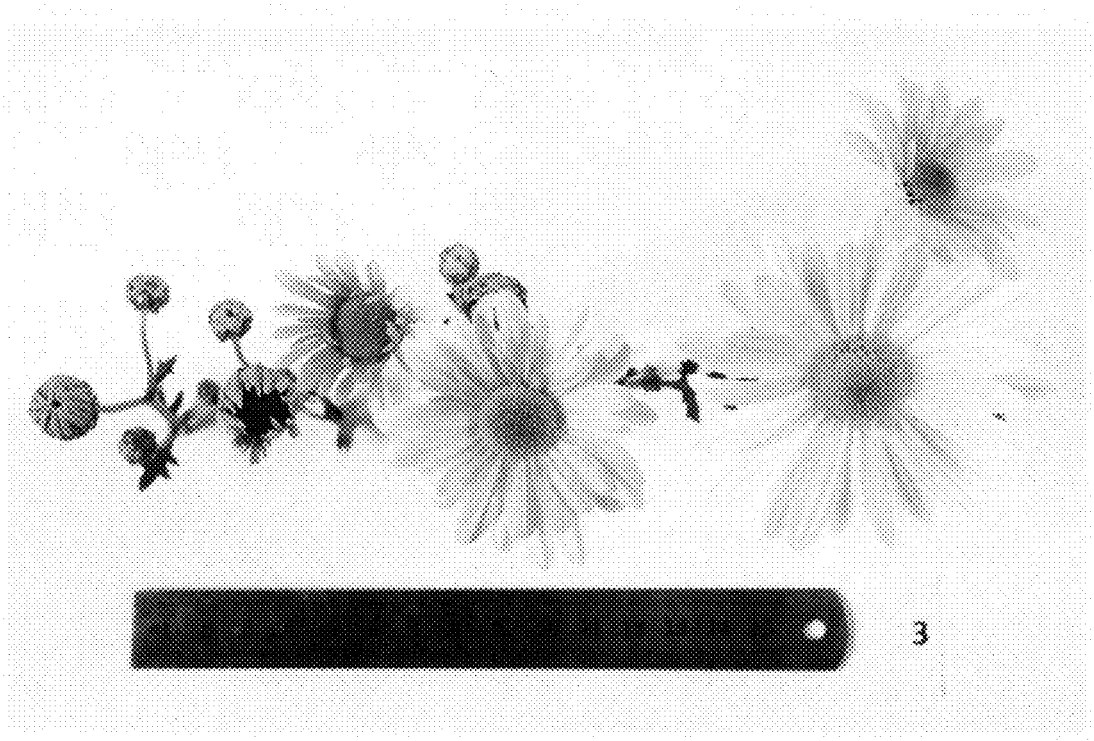
FIG. 2 shows the various stages of bloom of the new cultivar.
Figure 3:
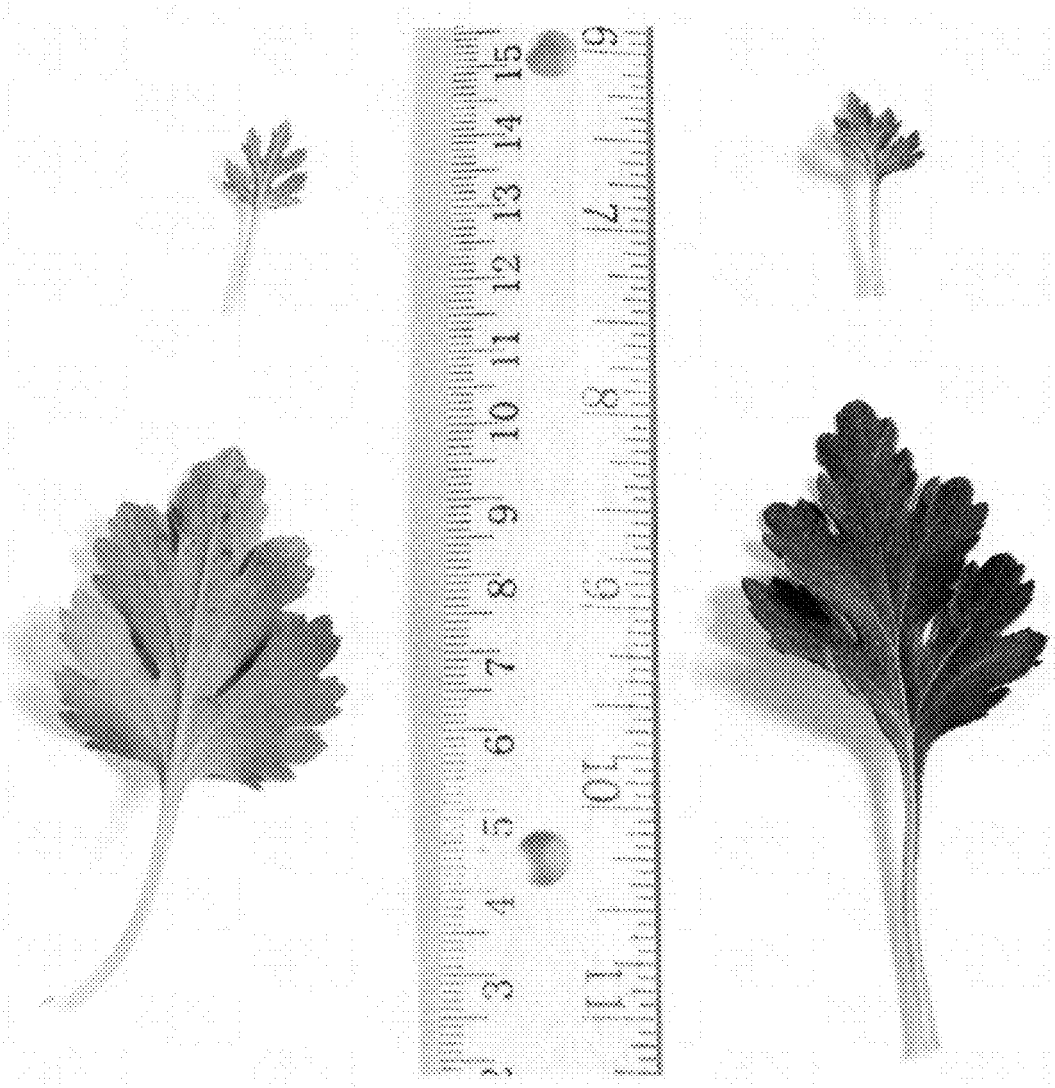
FIG. 3 shows the foliage of the new cultivar.

The plant descriptions and measurements were taken in St. Albans, Vt. in October 2010 under greenhouse conditions.

The aforementioned photographs were taken in a studio in St. Albans, Vt. in October 2010. The plants were started and grown in Coatesville, Pa., then shipped to St. Albans, Vt. in July 2010. Plants were grown under greenhouse conditions typical for herbaceous perennial plant production. Color references are made to The Royal Horticultural Society Colour Chart (R.H.S.) 2007.

TABLE 1

Difference between the new variety 'Autumn Moon' And 'Sheffield'

| | 'Autumn Moon' | 'Sheffield' |
|---|---|---|
| Flower Color: | Yellow | Pink |
| Flower Size: | 6.4-6.8 cm | 7-8 cm |
| Plant Height: | 34-39 cm | 60-75 cm |
| Bloom Time: | Oct-Nov | Sep-Oct |

Plant:
- *Form, growth and habit.*—Herbaceous garden-type; medium and upright, freely branching. Suitable for garden and pot production.
- *Plant height.*—10-15 cm.
- *Plant height (inflorescence included).*—40-46 cm.
- *Plant width.*—36 cm.

Roots:
- *Number of days to initiate roots.*—6 days at 18 degrees C.
- *Number of days to produce a rooted cutting.*—12 days at 18 degrees C.
- *Type.*—Fine, fibrous, free branching.
- *Color.*—RHS N155A.

Foliage:
- *Arrangement.*—Alternate, simple.
- *Immature leaf color upper surface.*—RHS N137C.
- *Lower surface.*—RHS 138B.
- *Mature leaf color, upper surface.*—RHS 137B.
- *Lower surface.*—RHS 137C.
- *Length.*—5.5-6 cm.
- *Width.*—3.8-4.2 cm.
- *Shape.*—Ovate.
- *Base shape.*—Accuminate.
- *Apex shape.*—Mucronulate.
- *Margin.*—Palmately lobed, somewhat serrate.
- *Texture, upper surface.*—Glabrous.
- *Lower surface.*—Pubescent.
- *Color of veins, upper surface.*—RHS 139D.
- *Color of veins, lower surface.*—RHS 139D.
- *Petiole color.*—RHS 139D.
- *Length.*—7-8 cm.
- *Diameter.*—0.2-0.3 cm.
- *Texture, upper surface.*—Glabrous.
- *Lower surface.*—Pubescent.

Stem:
- *Quantity of main branches per* 2 year old 2 gallon plant.—25.
- *Quantity of leaves per branch.*—14-16.
- *Color of stem.*—RHS 146C.
- *Length of stem.*—34-39 cm.
- *Diameter.*—0.3-0.4 cm.
- *Length of internodes.*—1-1.5 cm.
- *Texture.*—Glabrous.
- *Color of peduncle.*—RHS 146C.
- *Length of peduncle.*—3-5 cm.
- *Peduncle diameter.*—0.2 cm.
- *Texture.*—Glabrous.

Inflorescence:
- *Type.*—Composite type, solitary inflorescence (decorative-type) borne terminally above the foliage, ray florets arranged acropetally on a capitulum.
- *Quantity of short days to flowering (response time).*—55 days.
- *Quantity of inflorescences per stem.*—14-16.
- *Lastingness of individual blooms on the plant.*—35 days.
- *Fragrance.*—Slight-none.

Bud: (just before opening/showing color):
- *Color.*—RHS 138B.
- *Length.*—1-1.5 cm.
- *Width.*—0.8-1.2 cm.
- *Shape.*—Oblate.

Immature inflorescence:
- *Diameter.*—3.5 cm.
- *Color of ray florets, upper surface.*—RHS 18C.
- *Lower surface.*—RHS 16D.

Mature inflorescence:
- *Diameter.*—6.4-6.8 cm.
- *Total diameter of disc.*—1.5 cm.

Ray florets:
- *Average quantity of florets.*—30-36.
- *Color of florets, upper surface.*—RHS 11D.
- *Lower surface.*—RHS 11D.
- *Length.*—3.4-3.6 cm.
- *Width.*—0.6-0.7 cm.
- *Shape.*—Oblong.
- *Apex shape.*—Irregularly rounded.
- *Margin.*—Entire.
- *Texture, upper surface.*—Papillose.
- *Lower surface.*—Papillose.

Disc florets:
- *Average quantity of florets.*—Approximately 220-270.
- *Color of florets.*—RHS 9B.
- *Length.*—0.7 cm.
- *Width.*—0.2 cm.
- *Shape.*—Tubular, elongated.
- *Apex shape.*—Accute, 5 pointed.

Phyllaries:
- *Quantity.*—About 18-22.
- *Color, upper surface.*—RHS 143B, with RHS 144B margins which become papery and opaque.
- *Lower surface.*—RHS 139C, with RHS 144B margins which become papery with age and opaque.
- *Length.*—0.8-1.1 cm.
- *Width.*—0.7-0.9 cm.
- *Shape.*—Lanceolate.
- *Apex shape.*—Acute.
- *Base.*—Fused.
- *Margins.*—Entire, becoming papery with age.
- *Texture, upper surface.*—Glossy and smooth.
- *Lower surface.*—Pubescent.

Reproductive organs:
- *Pistil.*—1.
- *Length.*—0.8 cm.
- *Style color.*—RHS N144C.
- *Stigma color.*—RHS 9A.
- *Stigma shape.*—Bi-parted.
- *Ovary color.*—RHS 145D.
- *Stamens.*—4.
- *Color of filaments.*—RHS N144C.
- *Length of filaments.*—0.3 cm.
- *Anther color.*—RHS 14A.
- *Anther length.*—0.1 cm.

*Anther shape.*—Oblong.
*Color of pollen.*—RHS 9A.
*Pollen amount.*—Moderate.
*Fertility seed set.*—Has not been observed on this hybrid.

Disease/pest resistance: Disease susceptibility or resistance has not been observed on this hybrid.

What is claimed is:

1. A new and distinct variety of *Chrysanthemum* plant named 'Autumn Moon', substantially as illustrated and described herein.

* * * * *